United States Patent [19]

Verriest

[11] 4,068,097

[45] Jan. 10, 1978

[54] REMOTE MONITORING SYSTEM

[76] Inventor: Albert H. L. Verriest, 33 rue de l'Orient, 1040 Brussels, Belgium

[21] Appl. No.: 707,587

[22] Filed: July 22, 1976

[30] Foreign Application Priority Data

July 22, 1975 France .................................. 75.22815
July 16, 1976 France .................................. 76.21860

[51] Int. Cl.² ............................................ H04M 11/00
[52] U.S. Cl. ...................................... 179/2 A; 179/5 R
[58] Field of Search .............. 179/2 R, 2 A, 5 R, 5 P, 179/2 AM

[56] References Cited

U.S. PATENT DOCUMENTS 3,611,363 10/1971 McCrea ................................. 179/5 R
3,634,624 1/1971 Glidden ................................ 179/5 R

FOREIGN PATENT DOCUMENTS 1,416,351 12/1975 United Kingdom ................ 179/2 A Primary Examiner—Kathleen H. Claffy
Assistant Examiner—Joseph A. Popek
Attorney, Agent, or Firm—Sughrue, Rothwell, Mion, Zinn and Macpeak

[57] ABSTRACT

A system is disclosed which enables isolated, ill or handicapped persons to have instantaneous and direct contact with a monitor. The system comprises subscriber telephone sets connected to a monitoring station through one or more concentrators. Means are provided to permit direct communication between any of the subscriber sets and the monitoring station by sending of an alarm signal without even the handset being lifted at the subscriber set, automatically sending the identification of the calling subscriber set and completing a conversation link between the calling subscriber set and the monitoring station under supervision of the monitoring station.

5 Claims, 1 Drawing Figure

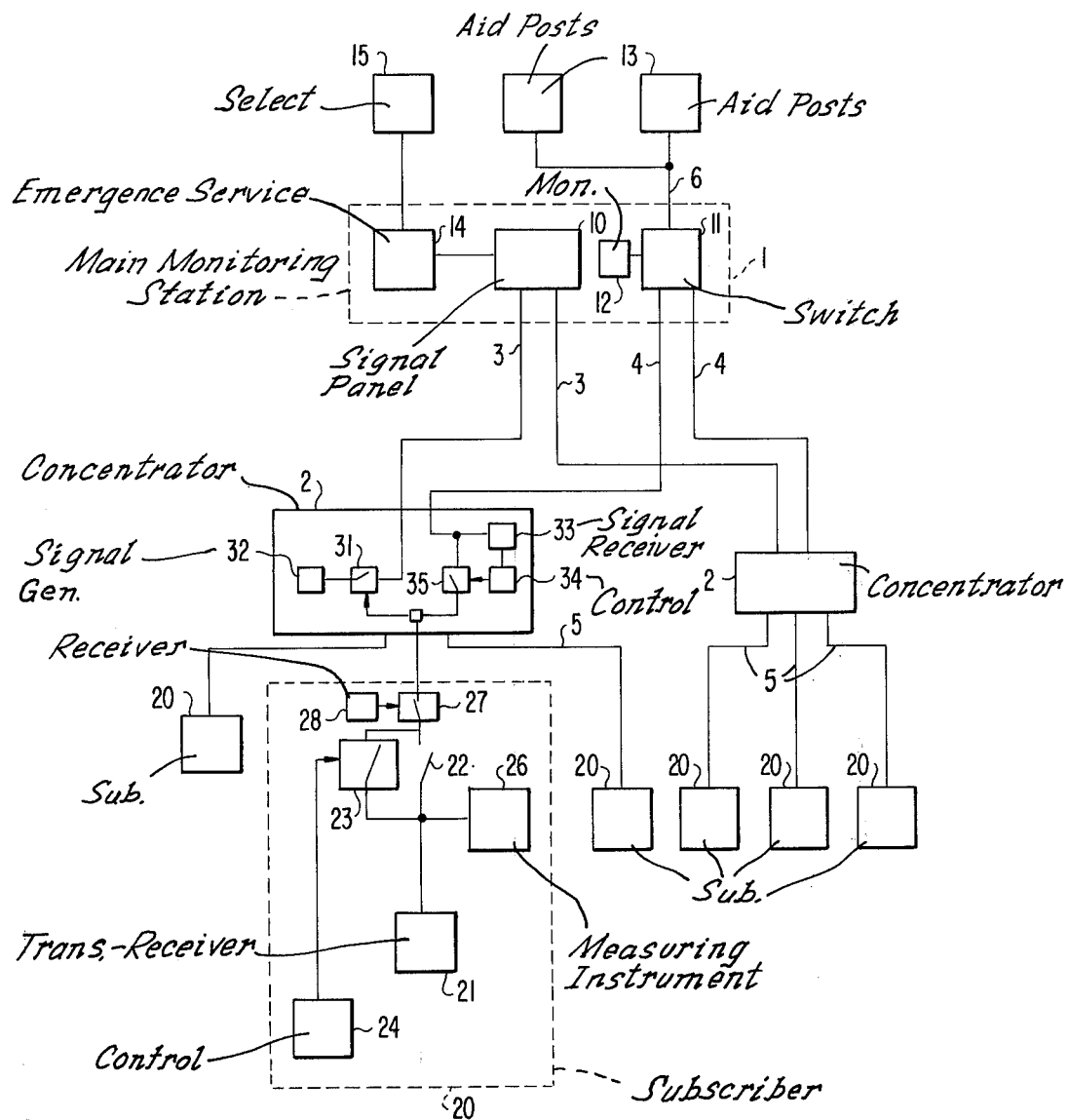

REMOTE MONITORING SYSTEM

This invention relates to a remote monitoring system intended in particular for people who are isolated, ill or handicapped.

This system enables these persons to have instantaneous and direct contact with a care and assistance service so as to receive prompt help and if necessary emergency aid without delay in cases of urgency such as illness, accident, fire, assault, etc.

The need for such a system is felt particularly in the case of isolated people whose state of health, while not requiring hospitalisation or constant attendance, necessitates regular monitoring.

This system comprises for each patient a telephone set arranged so as to be capable of being in direct communication with the monitoring station without even the handset being lifted and signal receiver means responsive to a signal having an ultrasonic, acoustic or radio frequency to disconnect the subscriber set from its telephone line during a short time interval such that an alarm signal is sent to the monitoring station. It may likewise comprise means for connecting up a measuring instrument, for example a thermometer, pulsimeter or analytical probe, in order to transmit automatically to the monitoring station signals which are representative of the measurements carried out.

The subscriber telephone sets are connected to one or more concentrators through individual telephone lines, each concentrator being in turn connected to the monitoring station through one signalling line and one conversation line. Each satellite station comprises means for sending to the monitoring station the identification of any of the subscriber sets connected thereto which has initiated an alarm call and for switching the calling subscriber line to the conversation line in response to a control signal from the monitoring station.

The monitoring station itself may be provided with a signalling device automatically receiving the identification of the calling sets and with a switching device for establishing telephone connections with the subscriber's sets on the one hand, with aid and assistance posts on the other hand, and for interconnecting a calling subscriber set to one of the aid or assistance posts. A card-index may be combined with the monitoring station, this latter then being provided with an index card selecting device.

One examplary embodiment of the system is represented diagrammatically in the attached drawing.

This embodiment comprises a main monitoring station 1 connected up to a given number of concentrators 2 by means of telephone lines comprising one or more signalling lines 3 and one or more conversation lines 4. In the drawing two concentrators have been shown; however, their number can of course be increased to any desired number. To each concentrator 2 there are connected a plurality of subscriber sets 20 by means of telephone lines 5. The connecting-up of the subscriber sets to concentrators has the sole purpose, in accordance with practice well known in the organisation of telecommunication networks, of distributing the traffic over a lesser number of long-distance communication lines. A subscriber set may consist of a conventional telephone set comprising a transmitter-receiver 21 and a switch represented by the circuit-breaker contact 22 of the conventional hooktype switch. In parallel with the switch 22 there is provided a second switch 23 actuated by a signal generated by a control device 24. The excitation of this latter has the effect of short-circuiting the conventional switch 22 so as to automatically connect the transmitter-receiver 21 to its individual telephone line 5. This control device 24 may comprise a simple bush-button on the set 20 or may be a transducer of any type producing an electric signal, for example, in response to a shock or a sound. This latter provision enables a person who is unable to operate his set to get in contact with the monitoring station by simply knocking against his telephone set for example.

A third normally closed switch 27 connected in series with the hook switch 22 is arranged to be actuated during a short time interval by a signal generated by a receiver means 28 responsive to an ultrasonic, acoustic or radio frequency. In case of using an ultrasonic or radio receiver, the control signal is generated by a pocket-size sender (not shown) which the patient can carry or keep at hand. In this way the patient is in a position to send an alarm signal from a distance in order to get from the monitor at the monitoring station the required emergency assistance.

Each concentrator 2 comprises means for sending to the monitoring station 1 through the signalling line 3 the identification of any of subscriber sets 20 which has initiated an alarm call and for bridging the calling subscriber line 5 to the conversation line 4 in response to a control signal from the monitoring station 1. The apparatus provided for each subscriber line is schematically represented in the left-hand block 2 for one subscriber line only. This apparatus substantially comprises switching means, signal generator means and receiver means.

As soon as a subscriber set 20 is bridged to its telephone line 5, either by excitation of the control device 24 or by excitation of the receiver means 28 or by setting the conventional hook-switch 22 in the offhook condition (i.e. by the handset being lifted), the signal appearing on the line 5 actuates a switching device 31 which connects the signal generator 32 to the signalling line 3. This generator then automatically sends on the line 3 to the monitoring station a characteristic signal, for example a signal with an acoustic frequency or a combination of frequencies, which identifies the calling subscriber set. When this identification signal is received at a signalling panel 10 in the monitoring station 1, the monitor with the aid of a switching device 11, causes a control signal to be sent on the line 4 to the concentrator involved. This control signal is received in a signal receiver means 33 which operates a control device 34 arranged for actuating switch means 35 thereby to interconnect the conversation line 4 and the calling subscriber line 5: the subscriber is thus able to converse with the operator (or monitor) and inform him of the mishap that has occurred with a view to obtaining assistance.

The subscriber set may be associated with various measuring instruments represented symbolically by the rectangle 26, such as a device for measuring the pulse, a thermometer, an analytical probe or the like. A switch means (not shown) is thus provided in the set circuit in order to connect these instruments with the telephone line and to send automatically to the monitoring station 1 a signal which is representative of the measurements so as to enable the monitoring station operator to immediately transmit them to a doctor or nurse to see whether they necessitate any treatment, or even urgent treatment.

The monitoring station 1 comprises a signalling panel 10 on which there appear indicators of sound-giving type, luminous type, direct reading or other types, which are actuated by the respective identification signals. As soon as an individual telephone line is established the identification of the set to which it is connected is thus automatically signalled.

The monitoring station 1 further comprises a switching device 11 connected, on the one hand, to the conversation lines 4 and, on the other hand, to a monitor telephone transmit/receive set 12 and through communication lines 6 to aid posts 13, at which there may be on duty doctors, nurses, welfare workers etc., and to emergency services 14 such as hospital, ambulance, police, fire-brigade. The monitoring station operator is thus able to answer a calling subscriber and to notify directly the service appropriate to the signalling case to be assisted. The switching device 11 likewise enables the operator to put the calling subscriber, when required, in oral contact with the official in charge of the appropriate service on duty. The user can thus receive immediate emergency assistance until the required aid service arrives on the scene. The switching device 11 also comprises means for interrupting the communication with the calling set and thus freeing the occupied conversation line 4, as well as means for holding a call. It will be noticed that only the signalling is under the control of the subscribers and that the occupation of the conversation lines is under the exclusive supervision of the monitoring station operator.

The monitoring station can likewise comprise a selection device 15 arranged so as to select the medical card of the calling subscriber. This device may be a manually controlled selector or more advantageously it may comprise a generator responding to the identification signal in order to send selection impulses to a card-index, so as to extract automatically therefrom the card corresponding to the calling subscriber. The operator of the monitoring station 1 can thus have immediately available basic information on the condition of the caller, so as to at once ascertain the seriousness of the particular caller's case and the nature of the appropriate services required by this case and so as to able to give the subscriber initial basic advice, at the same time informing the proper emergency or aid service as fully as possible on all the critical aspects of the case in question. To quote one example among many, the operator can in this way immediately ascertain whether the caller has a serious illness, such as a cardiac disorder, and can ascertain the degree of advancement of his state of health and also specific details regarding the therapies recommended for him and prohibited to him.

It is evident that various variants of the embodiment described may be conceived by the person skilled in the art. It is clear, for example, that if for any reason the provision of satellite stations is not recommended, it is no way obligatory and the subscriber sets can, on the contrary, quite simply be connected directly to the monitoring station 1 which could then comprise the switching and identification signal generating means otherwise provided in the satellite stations. It is also quite clear that the switches required in the system can be of the electronic type or of any other suitable type and that they do not necessarily have to be of the electromechanical type, even though these switches have for simplicity, been represented in the drawing by relay contacts.

Furthermore, the system is equipped with means for supervising and controlling its own circuits and elements so as to ensure the optimum reliability of the system.

What is claimed is:

1. A remote monitoring system comprising: a monitoring station, a plurality of subscriber telephone sets each having transmit-receive means and a hook-switch for connecting said transmit-receive means to an individual telephone line, at least one concentrator to which said telephone lines from the subscriber telephone sets are connected, said concentrator being connected to the monitoring station through a signalling line and a conversation line, said concentrator comprising, for each of said telephone lines connected thereto, a signal generator means for generating a respective identification signal, first switching means arranged for connecting the signal generator means to the signalling line in response to an alarm signal from the subscriber telephone set, and second switching means arranged for connecting the respective telephone line to the conversation line in response to a control signal from the monitoring station; and each subscriber telephone set further comprising third switching means connected in parallel with said hook-switch, control device means responsive to external excitation for actuating said second switching means to short circuit the hook-switch and thereby put the telephone set in the off-hook condition without the hook-switch having been manually actuated, fourth switching means connected in series between the hook-switch and the telephone line, said fourth switching means normally closed, and signal receiver means adapted to produce a control signal for actuating said fourth switching means in response to an excitation signal from a remote sender unit, thereby to disconnect the subscriber telephone set from the telephone during a short time and transmit an alarm signal.

2. A remote monitoring system according to claim 1, wherein the monitoring station comprises a signalling device connected to said signalling line and a fifth switching means connected on one side to said conversation lines and on the other side to a monitor transmit/receive set and to one or more aid posts thereby to enable the monitor at said monitoring station to interconnect any of said conversation lines and thus any of the subscriber sets with said monitor transmit/receive set and/or any of said aid posts.

3. A remote monitoring system according to claim 2, wherein the monitoring station is combined with a card-index and additionally comprises a selection device capable of sending a selection signal to said card-index to order to extract a card therefrom.

4. A remote monitoring system according to claim 3, wherein said selection device is a signal generator responsive to the detection of a given identification signal to produce a selection signal adapted to automatically extract a card from said card-index.

5. A remote monitoring system according to claim 1, wherein each of the subscriber telephone sets further comprises a device arranged to connect a measuring instrument with the corresponding telephone line and to apply thereto a signal which is representative of the measurement effected by such an instrument.

* * * * *